United States Patent [19]

Goeckel et al.

[11] Patent Number: 4,855,394
[45] Date of Patent: Aug. 8, 1989

[54] REACTION PRODUCTS AND CONDENSATES BASED ON SUBSTITUTED PROPYLENEUREAS AND THEIR PREPARATION

[75] Inventors: Ulrich Goeckel, Boehl-Iggelheim; Harro Petersen, Frankenthal; Rolf Osterloh, Gruenstadt; Eberhard Schupp, Schwetzingen; Werner Loch, Erpolzheim; Thomas Schwerzel, Ludwigshafen, all of Fed. Rep. of Germany

[73] Assignee: BASF Aktiengesellschaft, Ludwigshafen, Fed. Rep. of Germany

[21] Appl. No.: 302,131

[22] Filed: Jan. 25, 1989

Related U.S. Application Data

[63] Continuation of Ser. No. 886,403, Jul. 15, 1986, abandoned.

[30] Foreign Application Priority Data

Jul. 15, 1985 [DE] Fed. Rep. of Germany ....... 3525438
Jul. 15, 1985 [DE] Fed. Rep. of Germany ....... 3525434
Jul. 15, 1985 [DE] Fed. Rep. of Germany ....... 3525435
Jul. 15, 1985 [DE] Fed. Rep. of Germany ....... 3525437

[51] Int. Cl.$^4$ .................. C08G 71/02; C08G 12/12
[52] U.S. Cl. ........................... 528/263; 528/60; 528/61; 528/62; 528/64; 528/129; 528/164; 528/264; 528/289; 544/296
[58] Field of Search .............. 528/263, 264, 60, 61, 528/64; 544/296

[56] References Cited

U.S. PATENT DOCUMENTS

| | | | |
|---|---|---|---|
| 2,858,319 | 10/1958 | Benneville | 544/296 |
| 2,995,541 | 8/1961 | Kropa | 528/263 |
| 3,006,896 | 10/1961 | Horst | 528/263 |
| 3,684,811 | 8/1972 | Petersen | 544/296 |
| 3,763,106 | 10/1973 | Markiewitz | 528/263 |
| 3,772,225 | 11/1973 | Avis | 528/263 |
| 4,260,729 | 4/1981 | Schmidt | 544/296 |
| 4,262,121 | 4/1981 | Petersen | 544/296 |
| 4,340,743 | 7/1982 | Sandri | 544/296 |
| 4,349,663 | 9/1982 | Barsa | 544/296 |

FOREIGN PATENT DOCUMENTS 1303480  1/1973  United Kingdom ............. 3/74

Primary Examiner—C. Warren Ivy
Attorney, Agent, or Firm—Keil & Weinkauf

[57] ABSTRACT

Condensates based on substituted ureas, their reaction products with di- and/or polyisocyanates, derivatives of di- and/or polycarboxylic acids or p-substituted phenols and/or their methylol derivatives, their preparation and their use. These condensates each contain two or more cyclic urea units and can be prepared either by reacting primary di- or polyamines with ureas and reacting the product with predominantly CH-acidic aldehydes or by reacting primary amines with isocyanates and reacting the product with predominantly CH-acidic aldehydes in the presence of an acidic catalyst. The said condensates and their reaction products are useful for the preparation of heat-curable coating materials and of binders for cathodic electrocoating.

4 Claims, No Drawings

REACTION PRODUCTS AND CONDENSATES BASED ON SUBSTITUTED PROPYLENEUREAS AND THEIR PREPARATION

This application is a continuation of application Ser. No. 886,403, filed on July 15, 1986, now abandoned.

The present invention relates to condensates based on substituted propyleneureas which contain two or more cyclic urea units, reaction products of these condensates with di- and/or polyisocyanates, derivatives of di- and/or polycarboxylic acids or p-substituted phenols and/or their o-methylol derivatives, processes for their preparation, and their use as components in heat-curable coating materials.

Monocyclic propyleneureas are described in the literature, for example in Angew. Chem. 76 (1964), 909, Monatsheft Chem. 96 (1965) 1950 and German Pat. Nos. 1,230,805, 1,231,24 and 1,229,093.

N-Methylol derivatives and N-alkoxymethyl compounds of monocyclic propyleneureas possessing a hydroxyl or alkoxy function in the 4-position are used industrially as crosslinking agents for providing cellulose-containing textiles with a wrinkle resist finish or as components in surface coating binders. However, to effect crosslinking, products of this type require acidic catalysts at comparatively low temperatures. Particularly in industrial products, the presence of free formaldehyde and the liberation of formaldehyde during application and from the crosslinked substrates are disadvantages. The same applies to the use of aminoplast/formaldehyde resins, for example etherified urea/formaldehyde or melamine/formaldehyde resins, as crosslinking agents for surface coating binders. For curing, these systems once again require acid catalysis or comparatively high temperatures. For applications where crosslinking has to be carried out without acid catalysis, for example cathodic electrocoating, these resins can only be used in exceptional cases and at high curing temperatures above 180° C. The process, described in German Published Application DAS No. 2,057,799, for cathodic electrophoretic deposition of ionic, organic resins dispersed in water, comprises the use of blocked, multifunctional isocyanates as crosslinking components. The blocking agents which are stated therein and can be used in practice, such as aliphatic alcohols and, for example, caprolactam, require relatively high curing temperatures of above 180° C., the use of, for example, tin salts as crosslinking catalysts and a substantial loss of volatile, organic substances from the coating film during the curing process.

It is an object of the present invention to overcome these disadvantages and to provide resins which can be used in various fields and effectively crosslink macromolecular binders possessing suitable functional groups, e.g. hydroxyl or amino, in the absence of acidic catalysts and of heavy metal salts at comparatively low temperatures, without releasing toxic substances which pollute the environment, especially formaldehyde, amines, phenol or the like. We have found that this object is achieved by resin-like condensates based on propyleneureas containing 2 or more substituted propyleneurea units possessing a reactive group in the 4-position.

The present invention relates to condensates which essentially contain substituted propyleneureas of the general formulae (I) and/or (II)

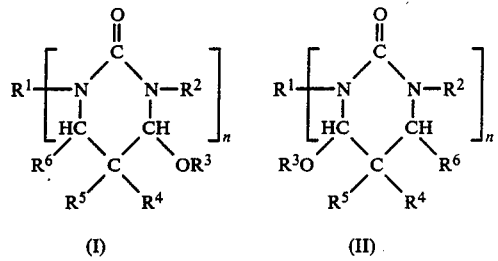

where $R^1$ is a divalent or polyvalent, straight-chain or branched alkylene, cycloalkylene, oxaalkylene or azaalkylene radical of 4 to 60 carbon atoms which may contain one or more hydroxyl groups and/or urea, carbamate, carboxamide or sulfonamide groups substituted by hydroxyalkyl, hydroxycycloalkyl, hydroxyoxaalkyl and/or hydroxyazaalkyl, $R^2$, $R^3$, $R^4$, $R^5$ and $R^6$ are identical or different and are each hydrogen, alkyl of 1 to 18 carbon atoms, cycloalkyl of 5 to 15 carbon atoms, aryl of 6 to 15 carbon atoms, aralkyl of 7 to 16 carbon atoms or oxaalkyl or azaalkyl, each of 2 to 18 carbon atoms, and $R^2$ may furthermore be hydroxyalkyl, with the proviso that where $R^2$ is hydroxyalkyl the latter is of 4 to 18 carbon atoms and the other radical or radicals $R^2$ are not aryl or aralkyl, and n is from 2 to 20, and the valency of $R^1$ corresponds to n and the individual radicals $R^2$, $R^3$, $R^4$, $R^5$ and $R^6$ of the n propyleneurea units of the formulae (I) and/or (II) may be identical or different while conforming to the stated definitions.

The present invention furthermore relates to a process for the preparation of these condensates, wherein first (a) primary di- and/or polyamines of the general formula (III)

are reacted with (b) urea or monosubstituted or symmetrically disubstituted ureas of the general formula (IV) $R^2NH-CO-NHR^2$ at from 100° to 200° C., in the presence or absence of an acidic or basic catalyst and of (c) dihydroxy compounds, polyhydroxy compounds, alkanolamines, hydroxyalkylcarboxylic acids and/or hydroxyalkylsulfonic acids or hydroxyalkylsulfonates, and the resulting products are reacted with (d) from 1.4 to 2.5 moles of one or more aldehydes of the general formula (V)

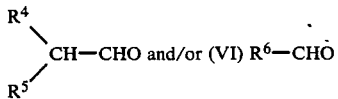

per mole of urea (b) in the presence of an acidic catalyst at from 50° to 150° C., in the presence or absence of a solvent, with the proviso that not less than 0.7 mole of an aldehyde (d) which contains one or more hydrogen atoms α to the aldehyde group is used per mole of urea (b) employed, $R^1$ to $R^6$ and n having the above meanings; and to a process for the preparation of these condensates, wherein (a) primary monoamines of the general formula (VII), $R^2$—$NH_2$, or primary di- and/or polyamines of the general formula (III)

$R^1$—$[NH_2]_n$ are first reacted with
(e) monoisocyanates of the general formula (VIII), $R^2$—NCO, or di- and/or polyisocyanates of the general formula (IX)

$R^1$—$[NCO]_n$ with the proviso that, where a primary monoamine $R^2$—$NH_2$ is used as component (a), this is reacted with di- and/or polyisocyanates $R^1$—$[NCO]_n$ and, where a monoisocyanate $R^2$—NCO is used as component (e), this is reacted with di- and/or polyamines $R^1$—$[NH_2]_n$ and the resulting di- or polyureas are reacted with (d) from 1.4 to 2.5 moles of one or more aldehydes

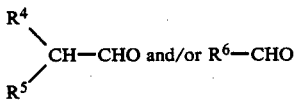

per mole of the urea units formed in the reaction of (a) with (e), in the presence of an acidic catalyst at from 50° to 150° C. and in the presence or absence of a solvent, with the proviso that not less than 0.7 mole of one or more aldehydes (d) which contain one or more hydrogen atoms α to the aldehyde group is used per mole of the urea units formed by reacting (a) with (e), $R^1$ to $R^6$ and n having the above meanings.

Isobutyraldehyde or a mixture of isobutyraldehyde with formaldehyde is preferably used as the aldehyde (d).

The present invention also relates in particular to reaction products of condensates which essentially contain substituted propyleneureas of the general formulae (I) and/or (II)

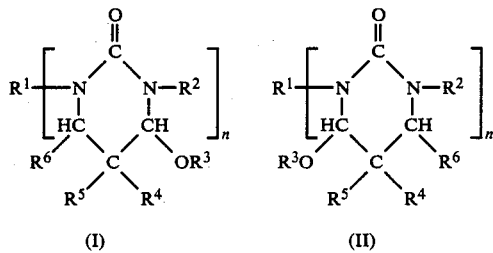

where $R^1$ is a divalent or polyvalent, straight-chain or branched alkylene, cycloalkylene, oxaalkylene or azaalkylene radical of 4 to 60 carbon atoms which may contain one or more hydroxyl groups and/or urea, carbamate, carboxamide or sulfonamide groups substituted by hydroxyalkyl, hydroxycycloalkyl, hydroxyoxaalkyl and/or hydroxyazaalkyl, $R^2$, $R^3$, $R^4$, $R^5$ and $R^6$ are identical or different and are each hydrogen, alkyl of 1 to 18 carbon atoms, cycloalkyl of 5 to 15 carbon atoms, aryl of 6 to 15 carbon atoms, aralkyl of 7 to 16 carbon atoms or oxaalkyl or azaalkyl, each of 2 to 18 carbon atoms, and $R^2$ may furthermore be hydroxyalkyl, with the proviso that where $R^2$ is hydroxyalkyl the latter is of 4 to 18 carbon atoms and the other radical or radicals $R^2$ are not aryl or aralkyl, and n is from 2 to 20, and the valency of $R^1$ corresponds to n and the individual radicals $R^2$, $R^3$, $R^4$, $R^5$ and $R^6$ of the n propyleneurea units of the formulae (I) and/or (II) may be identical or different while conforming to the stated definitions, with di- and/or polyisocyanates, derivatives of di- and/or polycarboxylic acids or p-substituted phenols and/or their o-methylol derivatives, with the proviso that, where o-methylolphenols are used, one or more of the radicals $R^1$ and $R^2$ of the formulae (I) and/or (II) contain a hydroxyl group or $R^2$ is hydrogen.

The present invention furthermore relates to a process for the preparation of these reaction products, wherein first
(a) primary di- and/or polyamines of the general formula (III)

$R^1$—$[NH_2]_n$ are reacted with
(b) urea or monosubstituted or symmetrically disubstituted ureas of the general formula (IV) $R^2NH$—CO—$NHR^2$ at from 100° to 200° C., in the presence or absence of an acidic or basic catalyst and of
(c) dihydroxy compounds, polyhydroxy compounds, alkanolamines, hydroxyalkylcarboxylic acids and/or hydroxyalkylsulfonic acids or hydroxyalkylsulfonates, and the resulting di- and/or polyureas are reacted with
(d) from 1.4 to 2.5 moles of one or more aldehydes of the general formula (V)

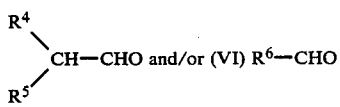

per mole of urea (b) in the presence of an acidic catalyst at from 50° to 150° C., in the presence or absence of a solvent, with the proviso that not less than 0.7 mole of an aldehyde (d) which contains one or more hydrogen atoms α to the aldehyde group is used per mole of urea (b) employed, $R^1$ to $R^6$ and n having the above meanings, and the products thus obtained are reacted with di- and/or polyisocyanates, derivatives of .id- and/or polycarboxylic acids or p-substituted phenols and/or their o-methylol derivatives, with the proviso that from 0.25 to 1.0 mole of isocyanate groups of the di- and/or polyisocyanate, acylhalide and/or anhydride groups or p-substituted phenol and/or its o-methylol derivative is used per mole of urea (b) employed; and to a process for the preparation of these reaction products, wherein
(a) primary monoamines of the general formula (VII), $R^2$—$NH_2$, or primary di- and/or polyamines of the general formula (III)

$R^1$—$[NH_2]_n$ are first reacted with (e) monoisocyanates of the general formula (VIII), $R^2$—NCO, or di- and/or polyisocyanates of the general formula (IX)

with the proviso that, where a primary monoamine $R^2$—$NH_2$ is used as component (a), this is reacted with di- and/or polyisocyanates

and, where a monoisocyanate $R^2$—NCO is used as component (e), this is reacted with di- and/or polyamines

and the resulting di- or polyureas are reacted with (d) from 1.4 to 2.5 moles of one or more aldehydes

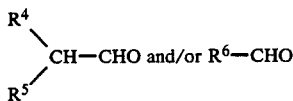

per mole of the urea units formed in the reaction of (a) with (e), in the presence of an acidic catalyst at from 50° to 150° C. and in the presence or absence of a solvent, with the proviso that not less than 0.7 mole of one or more aldehydes (d) which contain one or more hydrogen atoms α to the aldehyde group is used per mole of the urea units formed by reacting, (a) with (e), $R^1$ to $R^6$ and n having the above meanings, and the products thus obtained are reacted with di- and/or polyisocyanates, derivatives of di- and/or polycarboxylic acids or p-substituted phenols and/or their o-methylol derivatives, with the proviso that from 0.25 to 1.0 mole of isocyanate groups of the di- and/or polyisocyanate, acyl halide and/or anhydride groups or p-substituted phenol and/or its o-methylol derivative is used per mole of urea (b) employed.

Isobutyraldehyde or a mixture of isobutyraldehyde with formaldehyde is preferably used as the aldehyde (d).

The present invention furthermore relates to heat-curable coating materials which contain, as a binder, a mixture of (A) one or more polyadducts, polycondensates or polymers which have a mean molecular weight $\overline{M}_n$ of from 500 to 10,000 and possess on average two or more hydroxyl groups per molecule and may additionally possess primary and/or secondary and/or tertiary amino groups and (B) a reaction product or a condensate as hereinafter defined.

Preferred components (A) are polyester resins, reaction products of an epoxy resin with one or more amines, alcohols or mercaptans, and hydroxyl-containing polyacrylate resins.

The present invention furthermore relates to the use of these coating materials for solvent-containing baking finishes, the water-dilutable products obtainable from these by partial or complete neutralization with an acid, their use for the preparation of cathodic electro-coating finishes and for aqueous baking finishes, and an aqueous cathodic electrocoating bath which contains from 5 to 30% by weight of a novel coating material of this type.

Crosslinking is preferably effected by means of OH-containing macromolecular binders, with the formation of the corresponding acetalated structures, only water or the alcohol corresponding to the radical $R^3$ being liberated from the crosslinking agent during curing.

We have found, surprisingly, that the crosslinking reaction takes place even in the absence of acid catalysis, at very low temperatures of 100° C. or above, in the course of 20 minutes, and, for example, with conventional surface coating binders, gives solvent-resistant coatings or coating films which possess good mechanical strength. Crosslinking can be carried out in an acidic, neutral or alkaline medium, so that application can be effected not only from aqueous or solvent-containing systems but also by cathodic electrocoating. In spite of the high reactivity to hydroxyl-containing electrocoating binders, the combination of binder and the novel resins in aqueous or alcoholic solution possesses a surprisingly long shelf life of several months. The novel condensates are resin-like substances which have a molecular weight of, on average, from 300 to 3,000 and contain from 2 to 20, preferably from 2 to 10, substituted propyleneurea units. The properties of the products, such as solubility, compatibility, viscosity, flexibility and the like, can be varied over wide ranges by means of the substituents used.

In the general formulae (I) and/or (II), $R^1$ may be a divalent or polyvalent, straight-chain or branched alkylene, cycloalkylene, oxaalkylene or azaalkylene radical of 4 to 60, preferably 4 to 15, carbon atoms which contain one or more hydroxyl groups and/or urea, carbamate, carboxamide or sulfonamide groups substituted by hydroxyalkyl, hydroxycycloalkyl, hydroxyoxaalkyl and/or hydroxyazaalkyl, the valency of the radical $R^1$ being n.

Thus, $R^1$ can in principle be any organic group which is derived from, for example, a primary di- and/or polyamine or a polyfunctional isocyanate, e.g. 1,4-tetramethylene, 1,5-pentamethylene, 1,6-hexamethylene, 1,8-octamethylene, 1,10-decamethylene and similar radicals. $R^1$ may possess alkyl branches, e.g. 2-methyl-1,5-pentamethylene or 2,2,5-trimethyl-1,6-hexamethylene. Other suitable radicals are cycloalkylene groups, preferably those possessing from 5 to 8, in particular 6, ring members, e.g. cyclohexylene and 4,4'-dicyclohexyl-$C_1$–$C_8$-alkylenes, such as 4,4'-dicyclohexyl-2,2-propylene, 4,4'-dicyclohexylmethylene or its alkyl-substituted homologs. Other radicals $R^1$ which can advantageously be used are alkylene radicals which contain heteroatoms, e.g. 3,6-dioxa-1,8-octamethylene, 3,6,9-trioxa-1,11-undecamethylene, 2,5,8-trimethyl-3,6-dioxa-1,8-octamethylene, etc., which are derived from oligomers of ethylene oxide, propylene oxide and the like. N-Containing radicals may be, for example, 3-(2-ethylene)-3-aza-1,5-pentamethylene and 3-methyl-3-aza-1,5-pentamethylene, as well as those which contain both oxygen and nitrogen, preferably tertiary nitrogen, in the alkylene chain. $R^1$ may furthermore contain functional groups, for example hydroxyl groups or urea, carbamate, carboxamide or sulfonamide groups, each of which contains 2 to 12 carbon atoms in the alkyl group and is substituted by hydroxyalkyl, hydroxycycloalkyl, hydroxyoxaalkyl and/or hydroxyazaalkyl.

Examples of these are 3-[N'-butyl-N'-2-hydroxyethylureidoeth-2-yl]-3-aza-1,5-pentamethylene, 3-[N'-(2-hydroxyethoxyethyl)-ureidoeth-2-yl]-3-aza-1,5-pentamethylene and 4-[4-hydroxybutyramidoeth-2-yl]-4-aza-1,7-heptamethylene.

$R^2$, $R^3$, $R^4$, $R^5$ and $R^6$ are identical or different and are each hydrogen, alkyl of 1 to 18 carbon atoms, cycloalkyl of 5 to 15 carbon atoms, aryl of 6 to 15 carbon atoms, aralkyl of 7 to 16 carbon atoms or oxaalkyl azaalkyl, each of 2 to 18 carbon atoms, with the proviso that, where $R^2$ is hydroxyalkyl, the latter is of 4 to 18 carbon atoms and the other radical or radicals $R^2$ are not aryl or aralkyl. The structures of the general formula (I) and/or (II) can thus contain propyleneurea units having a similar or different pattern of substitution. $R^2$ cannot be an aromatic radical, such as phenyl, substituted phenyl, etc., or aralkyl, such as benzyl. Otherwise, it may have the meanings of the radicals $R^3$ to $R^6$, i.e. hydrogen or straight-chain or branched alkyl, e.g. methyl, ethyl, n- or isopropyl, n- or isobutyl, n-pentyl, n-hexyl or 2-ethylhexyl.

$R^4$ and $R^5$ are preferably short-chain, unbranched alkyl radicals, while $R^6$ is preferably hydrogen. However, cycloalkyl radicals, such as cyclohexyl and its alkyl-substituted homologs, aryl radicals, such as phenyl, aralkyl radicals, such as benzyl, 2-ethylphenyl and the like, are in principle also suitable. The substituents $R^2$ to $R^6$ can contain oxygen and/or nitrogen, preferably tertiary nitrogen.

Examples of these are 1- and 2-methoxyethyl, 2-methoxyprop-1-yl and N,N-dimethylaminoethyl. $R^2$ to $R^6$ may furthermore contain hydroxyl groups, but $R^2$ must possess 4 or more carbon atoms. An example of this is 2-hydroxyethoxyethyl. Other suitable radicals $R^3$ to $R^6$ are 2-hydroxyethyl, 2- and 3-hydroxypropyl, N,N-dimethyl-4-hydroxyethoxyaminoethyl and the like.

The novel condensates can therefore be prepared in different ways. Thus, di- and/or polyureas whose synthesis is described in principle in the literature are generally used as starting materials. Examples of these are given in Houben-Weyl, Vol. VIII, page 149 et seq.

For example, reacting suitable primary di- and/or polyamines, whose structures are defined by the radical $R^1$, with ureas gives the corresponding di- and/or polyureas. The particular amine can be reacted with urea itself, monosubstituted ureas and/or symmetrically disubstituted ureas possessing $C_1$-$C_4$-alkyl substituents, e.g. butylurea or N,N'-dimethylurea, at from 100° to 200° C., preferably from 120° to 170° C., for from 2 to 18, preferably from 4 to 8, hours. In general, from 1.0 to 1.5 moles of the particular urea are employed per primary amino group of the amine. The use of a larger molar excess makes it necessary to isolate the polyurea before the subsequent reaction and should therefore be avoided.

The substituents of the urea used thus provide the substituent(s) $R^2$ of the novel condensates. In the presence of the hydroxy compounds (c), the reaction gives di- and/or polyureas which contain further urea units, for example those substituted by hydroxyalkyl, or hydroxyl-containing carboxamide, carbamate or sulfonamide groups. This makes it possible to increase the molecular weight or incorporate functional groups capable of further reaction. The formation of di- and/or polyureas which has been described can be carried out in the absence of a solvent or in the presence of an inert solvent, e.g. xylene, under atmospheric, reduced or superatmospheric pressure.

The stated di- and/or polyureas can furthermore be obtained in a conventional manner by reacting monoisocyanates with primary di- and/or polyamines or reacting di- and/or polyisocyanates with primary amines. For example, amines from which the radical $R^1$ is derived and isocyanates from which the radical $R^2$ is derived, or vice versa, give products which are substantially similar to those obtained in the preparation process described above. The reaction is preferably carried out in an aqueous medium at from 0° to 120° C., preferably from 20° to 80° C., for from 0.5 to 6, preferably from 1 to 3, hours. In general, from 0.8 to 1.1 moles of isocyanate groups are reacted per mole of primary amino group. The resulting di- and/or polyureas are, as a rule, precipitated from the reaction mixture as relatively pure, crystalline solids and can, if required, be isolated by filtration, whereas the products obtained by the above process are predominantly resin-like.

The products obtained by both processes can be reacted further in a one-vessel process, even without further purification. The reaction is carried out using from 1.4 to 2.5 moles of one or more aldehydes per mole of urea units employed, but it is essential to use not less than 0.7 mole of one or more aldehydes which possess one or more acidic hydrogen atoms α to the aldehyde group. Examples of these are acetaldehyde, propionaldehyde, butyraldehyde, isobutyraldehyde, 2-methylbutanal and phenylacetaldehyde.

The pattern of substitution of these aldehyde components corresponds to the two radicals $R^4$ and $R^5$, and, if appropriate, $R^6$. Any further aldehyde component which may be present, and which provides the radical $R^6$, can be selected substantially freely and may be, for example, formaldehyde, pivalaldehyde, hydroxypivalaldehyde, benzaldehyde, furan-2-carbaldehyde, thiophene-2-carbaldehyde and the like.

Isobutyraldehyde or a mixture of formaldehyde and isobutyraldehyde is preferably used. The acetals of the stated aldehydes with $C_1$-$C_6$-alcohols or glycols, such as ethylene glycol, propylene 1,2-glycol, propane-1,3-diol, etc., can also be employed if the reaction is carried out in a preferred aqueous medium or in a $C_1$-$C_6$-alcohol. However, other suitable solvents are inert solvents, and liquid organic carboxylic acids, such as formic acid or acetic acid, are also advantageously used. The cyclocondensation of the stated di- and/or polyureas with the aldehydes described is carried out in the presence of an acidic catalyst, for example a mineral acid, such as hydrochloric acid, sulfuric acid or phosphoric acid, or a strong organic acid, such as formic acid or oxalic acid. Other suitable catalysts are acidic ion exchangers. In an advantageous procedure, a solution or suspension of the urea and aldehyde components is heated to the reflux temperature, but to no higher than 80° C., and the acid is then added a little at a time. However, it is also possible for the urea component, the acidic catalyst and, if required, the more sparingly volatile aldehyde component to be initially taken and the lower boiling aldehyde component or the aldehyde mixture to be added a little at a time at the reflux temperature, but at no higher than 80° C.

As a rule, the reaction is exothermic and is carried out until the aldehydes have been completely converted, advantageously at the resulting boiling point, but at no higher than 150° C. A temperature of from 60° to 120° C. is preferred. The reaction time required is from 0.5 to 4 hours.

The reaction may also be carried out under superatmospheric pressure of up to about 5 bar.

If the reaction is effected in an aqueous medium or without removal of the water of reaction, $R^3$ should be hydrogen. In the presence of an alcohol whose radical has the stated meanings of $R^3$, removal of the water of reaction makes it possible to prepare the particular hemiacetal.

To work up the mixture, the acid used for catalysis is neutralized, extracted, distilled off or, if appropriate, filtered off, these steps being carried out in a conventional manner. The resulting di- and/or polypropyleneureas are obtained as pale yellow, resin-like products, some of which are soluble in water and others in aromatic hydrocarbons, such as toluene or xylene, but most of which are soluble in alcohols and can therefore be obtained and purified in, for example, butanolic solution. The particular resin solution is finally brought to a solids content which depends on the intended use and the viscosity of the product and is generally from 60 to 80% by weight.

Where the condensates are reacted with di- and/or polyisocyanates, the substituted propyleneureas which contain structures of the stated formulae (I) and/or (II) are bonded, via free hydroxyl groups in the radicals $R^1$ and/or $R^2$, to di- and/or polyisocyanates with the formation of urethane structural units, from 0.8 to 1.2 moles of isocyanate groups preferably being used per mole of propyleneurea condensate of the formula (I) and/or (II). This gives bridged structures in which the radicals of the di- and/or polyisocyanates used act as bridge members. These radicals may be, for example, tetramethylene, hexamethylene, isophorone, diphenylmethane, toluylene, naphthylene and the like. Other substances which are suitable for the reaction with the stated propyleneureas are di- and/or polyisocyanates which can be produced from the above diisocyanates by dimerization (e.g. via urethdione formation), trimerization (e.g. via isocyanurate formation) or reaction with aliphatic diols or, if desired, alcohols having a fairly high OH functionality, such as ethylene glycol, diethylene glycol, propanediol, butanediol, hexanediol, neopentylglycol, trimethylolpropane, glycerol, pentaerythritol, trimethylolbenzene and the like.

The condensates are generally dissolved in an organic solvent which is inert to isocyanate groups, e.g. a chloroalkane, an aromatic hydrocarbon, a ketone, an ester or a mixture of these, any water or alcohol present is distilled off and the diisocyanate or polyisocyanate is then added. The reaction, which is initially exothermic, is controlled by cooling so that the reaction mixture is at no more than 50° C. When addition of the isocyanate is complete, the mixture is heated at from 60° to 80° C. until conversion of the isocyanate is complete, which takes from 0.5 to 2 hours.

The inert solvent used can, if required, be distilled off, leaving behind a pale yellow resin-like product which can then be taken up in a suitable solvent, such as an alcohol or aromatic hydrocarbon, and purified. The particular resin solution is finally brought to a solids content which depends on the intended use and the viscosity of the product and is generally from 60 to 80% by weight.

Where the condensates are reacted with derivatives of di- and/or polycarboxylic acids, the substituted propyleneureas of the stated formulae (I) and/or (II) are bonded, via free hydroxyl groups in the radicals $R^1$ and/or $R^2$, to reactive derivatives of di- and/or polycarboxylic acids with ester formation, from 0.25 to 1.0 mole of acyl halide groups and/or anhydride groups preferably being employed per mole of urea (b) used. This gives bridged structures in which the radicals of the di- and/or polycarboxylic acid derivatives used act as bridge members. For example, halides, such as chlorides and bromides, and/or anhydrides of aliphatic and/or aromatic di- and/or polycarboxylic acids, e.g. succinic acid, glutaric acid, adipic acid, sebacic acid, pimelic acid, suberic acid, dimeric fatty acids, terephthalic acid, phthalic acid, trimellitic acid or 1,2,4,5-benzenetetracarboxylic acid, can be used.

For further esterification of the alcoholic hydroxyl groups bonded in the propyleneurea resin, the di-and/or polypropyleneureas formed, advantageously in a very substantially anhydrous and alcohol-free state, are reacted with the relevant acyl halide, preferably acyl chloride or anhydride, in an inert solvent, with the addition of catalyst. The esterification is particularly preferably carried out using 1,2,4,5-benzenetetracarboxylic dianhydride in solution in acetic acid. The reaction is carried out at from 60° to 100° C. in the course of from 2 to 4 hours. When the reaction is complete, the solvent is removed and the residue is converted to, for example, a butanolic solution, and the latter is washed acid-free and salt-free in a conventional manner and brought to the desired solid resin content. The particular resin solution is finally brought to a solids content which depends on the intended use and on the viscosity of the product and is generally from 60 to 80% by weight.

Where the condensates are reacted with p-substituted phenols and/or their o-methylol derivatives, the substituted propyleneureas of the stated formulae (I) and/or (II) are bonded, via free hydroxyl groups in the radicals $R^1$ and $R^2$, to o-methylol derivatives of p-substituted phenols with formation of methylene ether groups, or via the nitrogen atom of propyleneurea units, in which $R^2$ is hydrogen, to o-methylolphenols, with formation of N-methylene-C groups, or via a C—C bond of the $C_4$ carbon atom of propyleneurea units to phenolic o-carbon atoms. This gives bridged structures in which the radicals of p-substituted phenols and/or their o-methylol derivatives act as bridge members. Examples of phenols used are p-alkylphenols, such as p-cresol, p-ethylphenol, p-octylphenol, p-nonylphenol, 4,4'-dihydroxydiphenylmethane, bisphenol A and similar compounds, as well as their o-methylol derivatives which preferably have a very high degree of o-methylolation.

The acid used for catalysis is partially neutralized, and, to effect further reaction, the appropriate phenol or o-methylolphenol and a solvent which forms an azeotropic mixture with water, preferably toluene or xylene and in particular n- or i-butanol, are added. Any residual water present and water of reaction are advantageously distilled off azeotropically, a pH of from 1.5 to 6, preferably from 2.5 to 4.5, and a temperature of from 60° to 120° C., preferably from 70° to 100° C., being maintained. When the water has been removed, the mixture is neutralized and washed salt-free and the resin solution is concentrated, these steps being carried out in a conventional manner.

The amount of phenol or o-methylolphenol is chosen so that from 0.25 to 1 mole of reactive phenolic o-positions or o-methylol groups are used per mole of urea (b) employed.

The particular resin solution is finally brought to a solids content which depends on the intended use and on the viscosity of the product and is generally from 60 to 80% by weight. When the novel condensates or their reaction products are used as components in heat-curable coating materials, the binder employed is a mixture of (A) one or more polyadducts, polycondensates or polymers which have a mean molecular weight $\overline{M}_n$ of from 500 to 10,000 and possess on average two or more hydroxyl groups per molecule and may additionally possess primary and/or secondary and/or tertiary amino groups and (B) a reaction product as claimed in claim 1 or a condensate as claimed in claim 2.

These coating materials can be used for solvent-containing or aqueous baking finishes and for the preparation of cathodic electrocoating finishes.

The condensates according to the invention are used in heat-curable coating materials by mixing them, as component (B), with a binder component (A) and, if required, with a suitable solvent.

Component (A) may be a polyadduct, polycondensate or polymer having a mean molecular weight $\overline{M}_n$ of from 500 to 10,000 and may be selected from a very wide variety of classes of compounds. The only important factor is that they possess on average two OH groups and, if required, primary and/or secondary and/or tertiary amino groups. Examples of suitable materials are polyesters, alkyd resins, polyethers, polyacrylate resins, polyurethanes, epoxy resins and their reaction products with alcohols, mercaptans or amines. Another suitable class of compounds comprises polydiene resins and polydiene oils, e.g. polybutadiene oils. In these substances, OH groups can be introduced at some of the double bonds, for example by an addition reaction with mercaptoethanol. Another possible method of introducing OH groups comprises reaction with maleic anhydride and then with OH-containing amines, such as ethanolamine or diethanolamine. The required derivative formation can also be effected by epoxidation of the polybutadiene oils with peracids, followed by reaction with amines.

Suitable polyesters are those which have a mean molecular weight $\overline{M}_n$ of from 500 to 10,000 and a hydroxyl number of from 25 to 400 and are obtained from aliphatic and/or aromatic dicarboxylic acids of from 4 to 10 carbon atoms, e.g. succinic acid, glutaric acid, adipic acid, pimelic acid, suberic acid, azelaic acid, sebacic acid, cyclohexanedicarboxylic acid, phthalic acid, isophthalic acid or terephthalic acid, or their derivatives and polyhydric alcohols, such as aliphatic diols, e.g. ethylene glycol, diethylene glycol, triethylene glycol, polyethylene glycol, propanediol, butanediol, hexanediol, neopentylglycol or neopentylglycol hydroxypivalate, and, if required, alcohols possessing a fairly high OH functionality, such as trimethylolpropane, glycerol, erythritol, pentaerythritol, trimethylolbenzene or trishydroxyethyl isocyanurate.

Suitable alkyd resins have a similar composition but contain one or more monocarboxylic acids, such as fatty acids. Alkyd resins which contain glycidyl esters of branched carboxylic acids may also be used.

Examples of suitable polyethers are aliphatic and araliphatic polyethers which are obtained by reacting dihydric and/or polyhydric alcohols with various amounts of ethylene oxide and/or propylene oxide.

Suitable polyacrylates are OH-containing polyacrylates having a hydroxyl number of from 25 to 500, an acid number of <25, preferably <10, and a Fikentscher K value (3% strength in acetone) of from 10 to 40, preferably from 12 to 25. They can contain, for example, the following monomers as copolymerized units: from 10 to 100, preferably from 20 to 40, % by weight of one or more OH-containing or NH-containing monomers, e.g. isopropylaminopropylmethacrylamide, or hydroxy-$(C_2-C_4)$-alkyl esters of an $\alpha$, $\beta$-ethylenically unsaturated carboxylic acid, e.g. 2-hydroxyethyl or hydroxypropyl (meth)acrylate or butanediol mono(meth)acrylate, and from 0 to 90, preferably from 60 to 80, % by weight of one or more ethylenically unsaturated carboxyl-free and hydroxyl-free compounds, for example vinylaromatics, such as styrene and vinyltoluene, vinyl esters of carboxylic acids of 2 to 18 carbon atoms, such as vinyl acetate and vinyl propionate, vinyl ethers of monoalkanols of 1 to 18 carbon atoms, such as vinyl methyl ether and vinyl isobutyl ether, esters of acrylic acid or methacrylic acid with $C_1-C_{12}$-monoalkanols, the corresponding diesters of maleic acid, of fumaric acid and of itaconic acid, (meth)acrylamide, (meth)acrylonitrile, monomers containing tertiary amino groups, such as diethylaminoethyl acrylate or diethylaminoethylacrylamide, or mixtures of these monomers. Another possible method of obtaining basic acrylates is to use epoxide-containing monomers, such as glycidyl methacrylate, and to add amines at the oxirane rings of the polymers.

Suitable polyurethanes are OH-containing polyurethanes which have a hydroxyl number of from 25 to 600 and are obtainable from aliphatic and/or aromatic diisocyanates, e.g. tetramethylene diisocyanate, hexamethylene diisocyanate, isophorone diisocyanate, diphenylmethane diisocyanate, toluylene diisocyanate, naphthylene diisocyanate or 4,4'-diphenyl ether diisocyanate, and, if appropriate, dimers or trimers derived from these, and aliphatic diols, such as ethylene glycol, diethylene glycol, triethylene glycol, polyethylene glycols, propanediol, butanediol, hexanediol, neopentylglycol or neopentylglycol hydroxypivalate, and, if required, alcohols having a fairly high OH functionality, such as trimethylolpropane, glycerol, pentaerythritol, trimethylolbenzene or trishydroxyethyl isocyanurate.

Examples of suitable epoxy resins are glycidyl ethers, such as those prepared from 2,2-bis-(4-hydroxyphenyl)-propane and epichlorohydrin. These epoxy resins may be further modified, for example by reaction with polyfunctional alcohols or SH compounds. Examples of such polyfunctional alcohols which are suitable for effecting modification are ethylene glycol, 1,2-propylene glycol, 1,3-propylene glycol and butane-1,4-diol.

If elastification is desired, long-chain polyfunctional alcohols or mercaptans can also be employed. If these compounds are employed in amounts greater than equivalent amounts, based on the epoxide groups present, products possessing terminal OH or SH groups are formed. If, on the other hand, less than the equivalent amounts are used, the resulting products possess terminal epoxide groups and can, if desired, be reacted further. While the reaction of the mercaptans with epoxide groups takes place even in the absence of a catalyst, the reaction of the alcohols requires the use of a catalyst, e.g. dimethylbenzylamine, and elevated temperatures of about 50°–150° C.

Reaction products of epoxy resins with primary or secondary amines can likewise be used as component (A). The reaction with hydroxyl-containing amines, e.g. ethanolamine, methylethanolamine or diethanolamine, is particularly useful in this respect.

If the products used as component (A) contain amino groups in amounts sufficient to render the product water-soluble or water-dispersible after protonation with an acid, it is possible, in combination with component (B), to prepare water-dispersible binders for baking finishes, in particular binders which can be used for cathodic electrocoating. The above reaction products of epoxy resins with primary or secondary amines can be used for this purpose.

Many of the base resins suggested for cathodic electrocoating can also be used as component (A) in the novel coating materials, for example the reaction products of phenolic Mannich bases with epoxy resins as described in German Pat. No. 2,419,179, the reaction products of extended chain epoxy resins with secondary amines as described in U.S. Pat. No. 4,104,140, and reaction products of (meth)acrylamidomethylated phenols, amines and epoxy resins, for example those described in German Laid-Open Applications DOS No. 2,942,488 and DOS No. 3,021,300. The only considerations of importance are that they have a molecular weight of from 500 to 10,000 and possess on average two or more OH groups and primary and/or secondary amino groups per molecule. Regarding the crosslinking activity during baking, it is fully adequate if the component (A) contains only OH groups and no primary and/or secondary amino groups; however, it is frequently advantageous to use products which also contain primary and/or secondary amino groups since these permit the preparation of aqueous electrocoating baths having a high pH of, for example, from 6.5 to 8.0. A high pH, especially one in the region of 7 or higher, makes it possible to avoid plant corrosion. One possible method for obtaining products which possess primary and secondary amino groups and are useful as component (A) is to react excess primary diamines with epoxy resins and then separate off the excess amine at elevated temperatures and under reduced pressure.

Particularly suitable diamines for this purpose are those of 2 to 6 carbon atoms, e.g. ethylenediamine, 1,2- and 1,3-diaminopropane, 1,4-diaminobutane and hexamethylenediamine. The reaction products can, if desired, be subjected to a chain-extending reaction with a dicarboxylic acid, e.g. sebacic acid or a dimeric fatty acid. The desired molecular weight can be obtained by appropriately selecting the ratio of dicarboxylic acid to epoxy resin/amine adduct; for example, 1 mole of dimeric fatty acid can be used per two molecules of epoxy resin/amine adduct.

Another possible method of preparing products which possess primary amino groups and are useful as component (A) is to react epoxy resins with secondary amines which contain blocked primary amino groups. Examples of such amines are the diketimine of diethylenetriamine, the ketimine of aminoethylethanolamine and the ketimine of N-methylethylenediamine. The ketimines can be prepared in a simple manner from free amines and a ketone, e.g. methyl isobutyl ketone, with removal of water. During the reaction with epoxy resins, only the secondary amino group reacts, and the ketimine can then be cleaved by adding water, the free primary amino group being formed again.

By reacting some of the primary amino groups with a dicarboxylic acid, these products too can be elastified by chain extension.

The novel binder mixture contains component (A) in general in an amount of from 30 to 95, preferably from 60 to 85, % by weight, based on the total amount of the binder mixture.

Component (B) is used in general in an amount of from 5 to 70, preferably from 15 to 40, % by weight, based on the total amount of the binder mixture (A)+(B).

To prepare the coating materials according to the invention, components (A) and (B) are mixed. Components of low viscosity can be mixed as such and, if required, may be heated to no higher than 100° C. Products having a higher viscosity are dissolved in organic solvents prior to mixing. Conventional solvents, such as alcohols, ketones, esters, ethers, hydrocarbons, etc. can be used for this purpose.

The novel coating materials, if necessary with the addition of pigments, assistants and curing catalysts, can be applied onto substrates, such as wood, plastic or metal, by a conventional method, such as spraying, immersion, casting or knife-coating.

Products which, because of their content of amino groups, become water-dispersible after neutralization with an acid, e.g. acetic acid, can also be used in the form of an aqueous dispersion. Products of this type can advantageously be employed for electrocoating electroconductive substrates, such as metal articles, sheets, etc. made of brass, copper, aluminum, metalized plastics or materials coated with conductive carbon, and iron and steel, which may or may not have been chemically pretreated, e.g. phosphatized. For this purpose, an acid, e.g. formic acid, acetic acid or lactic acid, is stirred in to effect partial or complete neutralization, and the mixture is diluted with water to the processing concentration.

For cathodic electrocoating, a solids content of from 5 to 30% by weight is generally established. Deposition is usually effected at from 15° to 40° C. in the course of from 1 to 5 minutes at a pH of from 5.0 to 9, preferably from 6.5 to 8.0, and at a deposition voltage of from 50 to 500 volt. The electrically conductive article being coated is made the cathode. The film deposited is cured at above 100° C. for about 20 minutes.

The Examples which follow illustrate the invention without restricting it. In the Examples, parts and percentages are by weight, unless stated otherwise.

For the sake of clarity, only the formulae corresponding to structure type (I) are listed in each case, although the products described do of course include the possible isomers of structure type (II).

EXAMPLE 1

Preparation of a condensate which essentially contains structures of the formula

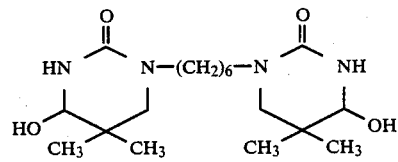

(1) 168 parts of hexamethylene diisocyanate are added dropwise to 350 parts of a 12% strength aqueous ammonia solution. The temperature is kept at 40° C. until addition of the isocyanate is complete, after which the mixture is stirred for 1 hour at 80° C. The precipitated bisurea is filtered off, washed neutral with hot water and then recrystallized to give 132 parts (65% of theory) of hexamethylenebisurea of melting point 197°–200° C.

(2) As described in Houben-Weyl, Vol. VIII, page 151, 115 parts of hexamethylenediamine and 180 parts of urea are heated at from 130° to 140° C. for from 3 to 4 hours, and the reaction product which solidifies is recrystallized from water.

101 parts of the hexamethylenediurea obtained as described in (1) or (2) are refluxed (at about 62° C.) for 20 minutes with 75 parts of 40% strength aqueous formaldehyde, 72 parts of isobutyraldehyde and 100 parts of water, while stirring. Thereafter, 72 parts of concentrated hydrochloric acid are added dropwise sufficiently rapidly to produce vigorous refluxing. The temperature increases to about 105° C. Stirring is then continued for 2 hours under reflux. The mixture is cooled to 60° C., after which the pH is brought to 6 with sodium hydroxide solution, water is removed, a mixture of 66 parts of isobutanol and 50 parts of methanol is added, the mixture is homogenized and salt is filtered off. 252 parts of a pale yellow, slightly viscous resin solution having a solids content of 57% are obtained.

EXAMPLE 2

Preparation of a condensate which essentially contains structures of the formula

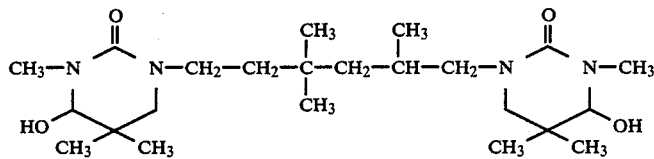

158 parts of 2,4,4-trimethylhexamethylene-1,6-diamine and 195 parts of N,N'-dimethylurea are heated to 120° C. and stirred at this temperature for 2 hours. During this procedure, nitrogen is passed continuously over the melt. Stirring is then continued for a further 2 hours at 160° C., after which 850 parts of water are added and the mixture is stirred for 30 minutes at from 80° to 100° C., while nitrogen is passed in. The mixture is cooled to 40° C., after which the water is decanted, 150 parts of 40% strength aqueous formaldehyde and 144 parts of isobutyraldehyde are added and the mixture is stirred for 15 minutes at the reflux temperature (68° C.). After the addition of 150 parts of concentrated hydrochloric acid, the reflux temperature increases to 104° C. Stirring is continued for 2 hours at this temperature, the mixture is neutralized with sodium hydroxide solution and the product is extracted with toluene. The toluene solution is extracted twice with water and concentrated to give 372 parts of a 79% strength yellowish brown solution of the resin in toluene.

EXAMPLE 3

Preparation of a condensate which essentially contains structures of the formula CH$_3$—N ⏜ N—(CH$_2$)$_6$—N ⏜ N—CH$_3$
i-C$_4$H$_9$—O ⏝ ⏝ O—i-C$_4$H$_9$
      CH$_3$  CH$_3$      CH$_3$  CH$_3$ 67 parts of hexamethylene diisocyanate are added dropwise to 62 parts of a 40% strength aqueous methylamine solution and 200 parts of water and, when the addition is complete, the mixture is stirred for 1 hour at 60° C. The precipitated urea is filtered off under suction, and 80 parts of it are introduced into a mixture of 50 parts of isobutyraldehyde and 76 parts of a 30% strength aqueous formaldehyde solution. The thick suspension is heated to 62° C., after which 15 parts of concentrated hydrochloric acid are added in the course of 1 minute.

The reflux temperature increases to 102° C., and this temperature is maintained for 90 minutes. The pH is then brought to 3–4 with sodium hydroxide solution, and 580 parts of isobutanol are added. Water is then separated off as completely as possible at from 70° to 80° C. under slightly reduced pressure, after which the mixture is neutralized to pH 7–7.5 with sodium hydroxide solution and isobutanol is removed until the viscosity of the solution is about 1500 mPa.s at 30° C. The solution is then filtered off from the salt to give 289 parts of a 75% strength solution of the resin in isobutanol.

EXAMPLE 4

Preparation of a condensate which essentially contains structures of the formula

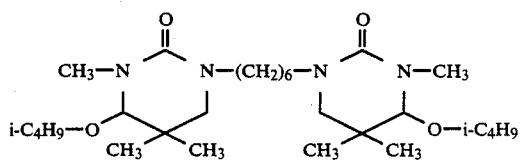

148 parts of 3,6-dioxaoctane-1,8-diamine and 193 parts of N,N'-dimethylurea are stirred at 130° C. and 135° C., for 1 hour in each case, and then at 140° C. for 2.5 hours, while nitrogen is passed in, until the elimination of about 60 parts of methylamine indicates that conversion is substantially complete.

280 parts of the resulting urea are mixed with 160 parts of a 40% strength aqueous formaldehyde and 153 parts of isobutyraldehyde, and the mixture is heated to 65° C. After the addition of 42 parts of concentrated hydrochloric acid, the reflux temperature increases to about 102° C. The mixture is stirred for 90 minutes at this temperature, after which it is neutralized with sodium hydroxide solution, water is distilled off and the residue is taken up with methanol. The solution is filtered off from the salt, methanol is distilled off and the residue is then diluted with water to a solids content of 50%. 840 parts of an aqueous resin solution having a viscosity of 13 mPa.s (20° C.) are obtained.

EXAMPLE 5

Preparation of a condensate which essentially contains structures of the formula

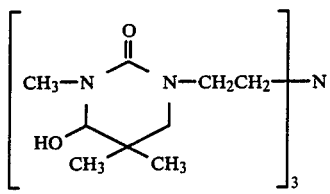

292 parts of tris-2-aminoethylamine and 528 parts of N,N'-dimethylurea are stirred at 120° C. and 140° C., for 1 hour in each case, then at 150° C. for 2 hours and finally at 160° C. for 0.5 hour, stirring being carried out under nitrogen. The viscosity of the reaction mixture increases substantially toward the end of the reaction. 350 parts of water and 50 parts of glacial acetic acid are then added, and the refluxed mixture is stirred for 1 hour under nitrogen. Thereafter, 450 parts of formaldehyde (40% strength in water) and 144 parts of concentrated nitric acid are added, and the mixture is heated to 65° C. 432 parts of isobutyraldehyde are then added dropwise sufficiently rapidly to keep the reaction mixture refluxing vigorously. The reflux temperature increases to about 103° C., and the mixture is stirred at this temperature for 2 hours. After the mixture has been cooled, the pH is brought to 8.1 with sodium hydroxide solution, and 800 parts of butanol and 120 parts of methanol are added. The aqueous phase is separated off and the organic phase is washed with water and concentrated under reduced pressure to give 1254 parts of a 74.5% strength resin solution.

EXAMPLE 6

Preparation of a condensate which essentially contains structures of the formula

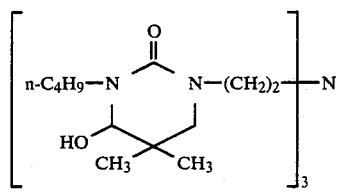

49 parts of tris-(2-aminoethyl)-amine are dissolved in 200 parts of acetone, and the solution is added dropwise to a mixture of 99 parts of n-butyl isocyanate in 200 parts of acetone. The temperature is initially kept at 40° C. by cooling with ice and, when the exothermic reaction is complete, is brought to 60° C. for 30 minutes. 200 parts of water are added, after which stirring is continued for a further 30 minutes at 80° C. and the trisurea is then filtered off under suction, washed with water and dried. The yield is 114 parts (77% of theory). The product is taken up in 200 parts of water, 50 parts of glacial acetic acid and 58 parts of formaldehyde (40% strength in water). 45 parts of concentrated nitric acid are added to give a clear solution, which is heated to about 60° C. During the dropwise addition of 55 parts of isobutyraldehyde, the reflux temperature increases to about 100° C. The mixture is stirred under reflux for 1 hour and then cooled, the pH is brought to 7 with sodium hydroxide solution, the product is taken up in 350 parts of toluene, the solution is washed twice with water and the organic phase is then concentrated to a solid resin content of 75% (viscosity about 2000 mPa.s).

EXAMPLE 7

Preparation of a condensate which essentially contains structures of the formula

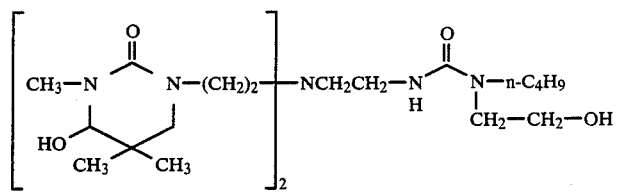

292 parts of tris-(2-aminoethyl)-amine, 120 parts of urea and 352 parts of N,N'-dimethylurea are continuously heated from 120° C. to 160° C. for 3.5 hours, while nitrogen is passed in. Thereafter, 214 parts of n-butylethanolamine are introduced and the mixture is stirred for a further 3 hours at from 140° to 160° C.

The residual volatile components are stripped off at 140° C. under reduced pressure. Thereafter, 400 parts of water, 100 parts of glacial acetic acid, 294 parts of formaldehyde (40% strength in water) and 283 parts of isobutyraldehyde are added and the mixture is refluxed (at about 62° C.). 230 parts of concentrated nitric acid are then added dropwise, the reflux temperature increasing to 103° C. Stirring is continued for 2 hours at this temperature. The mixture is cooled and neutralized with sodium hydroxide solution, after which 1200 parts of isobutanol are added and the organic phase is separated off, washed with water and concentrated to give 1140 parts of a 61.5% strength resin solution.

EXAMPLE 8

Preparation of a condensate which essentially contains structures of the formula

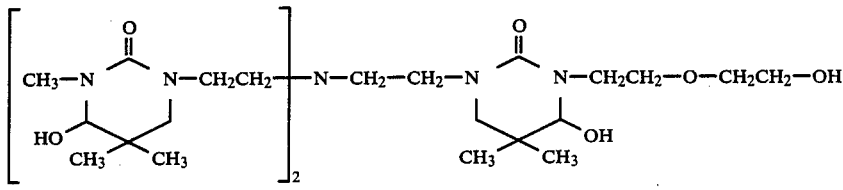

176 parts of N,N'-dimethylurea, 60 parts of urea and 146 parts of tris-2-aminoethylamine are heated from 120° to 160° C. in the course of 3.5 hours, after which 105 parts of 2,2-aminoethoxyethanol are added and heating is continued for a further 3 hours at temperatures increasing from 140° to 160° C. 200 parts of water and 50 parts of glacial acetic acid are then added. 225 parts of 40% strength aqueous formaldehyde solution and 216 parts of isobutyraldehyde are introduced, after which the mixture is refluxed and 150 parts of concentrated nitric acid are added in the course of 20 minutes. During this procedure, the reflux temperature increases to about 100° C. Stirring is continued for 2 hours at this temperature, and the mixture is cooled and neutralized with sodium hydroxide solution. To remove the salt, the reaction mixture is concentrated, the residue is taken up in methanol, the solution is filtered and concentrated again, and the pale yellow resin-like product is taken up in water. The yield is 924 parts (50% strength in water).

EXAMPLE 9

Preparation of a condensate which essentially contains structures of the formula

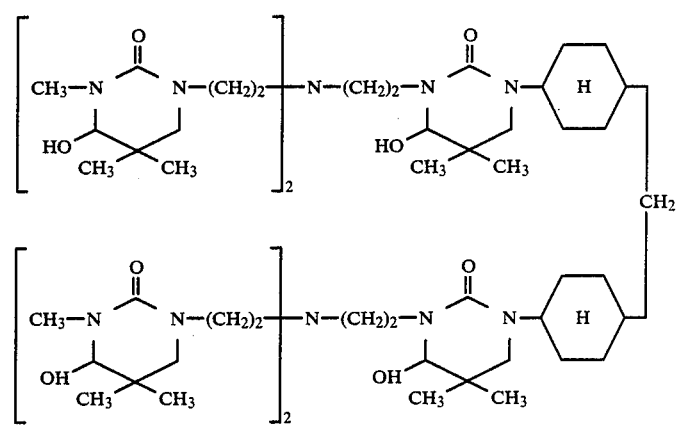

264 parts of N,N'-dimethylurea, 146 parts of tris-2-aminoethylamine and 101 parts of 4,4'-diaminodicyclohexylmethane are heated from 80° C. to 160° C. in the course of 5.5 hours, nitrogen being passed over the melt. 125 parts of water and 125 parts of glacial acetic acid are added rapidly, and the mixture is stirred under reflux for 1 hour. Thereafter, 214 parts of 40% strength aqueous formaldehyde and 205 parts of isobutyraldehyde are added, the mixture is heated to 65° C. and 210 parts of concentrated nitric acid are introduced very rapidly. The initially viscous reaction mixture attains a low viscosity again, and the reflux temperature increases to 104° C. The mixture is stirred for 2 hours at this temperature, the pH is brought to 6.5 with sodium hydroxide solution and the resin is extracted with 2000 parts of isobutanol. The solution of the resin in isobutanol is washed with water and concentrated to give 642 parts of a solution having a solids content of 63.5%.

EXAMPLE 10

Preparation of a condensate which essentially contains structures of the formula

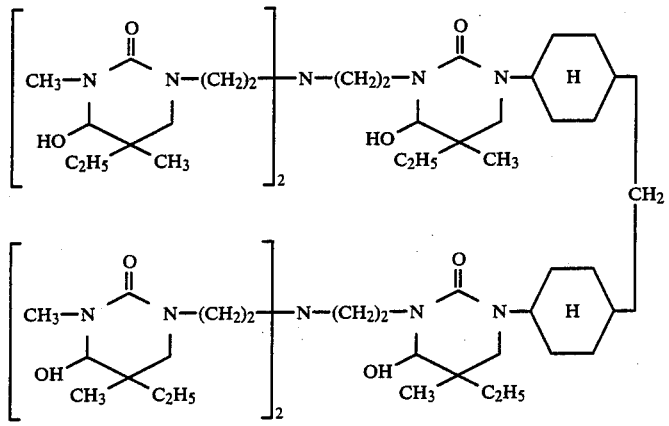

The procedure described in Example 9 is followed, except that 205 parts of isobutyraldehyde are replaced by 245 parts of 2-methylbutanal. 648 parts of a 64.5% strength solution of the resin in isobutanol are obtained.

EXAMPLE 11

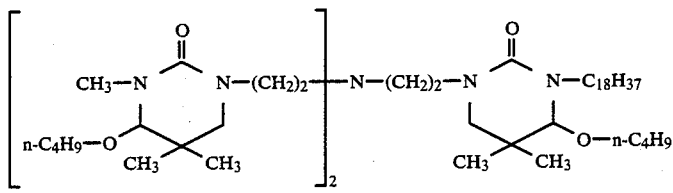

292 parts of tris-2-aminoethylamine, 528 parts of N,N'-dimethylurea and 538 parts of stearylamine are heated from 120° C. to 160° C. in the course of 5 hours and stirred under nitrogen. Thereafter, 2000 parts of butanol and 500 parts of concentrated hydrochloric acid are added and the mixture is brought to about 60° C. 180 parts of paraformaldehyde are added, after which the mixture is stirred for 15 minutes at 60° C., and 432 parts of isobutyraldehyde are then added dropwise so that the mixture refluxes vigorously. The temperature increases to 100°-102° C. during this procedure, and the reaction mixture becomes clear. Refluxing is continued for 2 hours, after which the mixture is neutralized with sodium hydroxide solution and filtered off from the salt, the butanol phase is washed twice with water and the organic phase is distilled to give 640 parts of a clear, slightly yellowish resin solution having a solids content of 55%.

USE EXAMPLE 1

A coating formulation is prepared from 70 parts (based on solids) of one of the surface coating binders A1 to A3 below and 30 parts (based on solids) of one of the novel condensates B1 to B4 described in Examples 1, 5, 7 or 9, or, for comparison, commercial products B5 to B8.

The mixture of the two components is brought to about 50-60% strength with ethanol and applied onto a steel sheet by means of a 100 μm knife coater.

The coatings are then baked for 20 minutes at the temperatures stated in the Table. The coating films are tested by rubbing them 100 times with a cottonwool ball soaked in acetone; the results are reproduced in Table I.

A1 Commercial polyester-based surface coating binder (e.g. Alkydal ® R40)

A2 Non-self-crosslinking, cathodic binder prepared by reacting 400 parts of hexamethylenediamine and 400 parts of an 80% strength solution of a commercial epoxy resin based on 2.2,-bis-(4-hydroxyphenyl)-propane in toluene at from 80° to 100° C. and distilling off toluene and excess amine until the amine number is 160 mg of KOH/g and the softening point about 100° C., and then reacting 400 parts of this adduct with 140 parts of a dimeric fatty acid, 17.5 parts of stearic acid, 59 parts of phenyl diglycol, 37 parts of benzyl alcohol, 9 parts of triphenyl phosphine, 43 parts of toluene and 12 parts of ethylene diamine at 170° C., with removal of water by distillation until an acid number of from 4 to 8 is reached, and then bringing the solids content to 70° with butyl glycol, ethanol and water in a weight in a weight ratio of 7:5:6.

A3 OH-containing polyacrylate prepared by copolymerization of 40 parts of butyl acrylate, 20 parts of styrene, 20 parts of methyl methacrylate, 15 parts of hydroxypropyl acrylate and 5 parts of acrylic acid and having a solids content of 26% in water, a K value of 25.7 and an acid number of 42 at a degree of neutralization of 70% with dimethylethanolamine.

B1 Novel condensate as described in Example 1.
B2 Novel condensate as described in Example 5.
B3 Novel condensate as described in Example 7.
B4 Novel condensate as described in Example 9.

For comparison

B5 Commercial melamine/formaldehyde surface coating resin, etherified with butanol (e.g. Luwipal ® 015).

B6

Commerical urea/formaldehyde surface coating resin, etherified with isobutanol (e.g. Plastopal ® FIB)

B7 Crosslinking agent based on β-hydroxyalkyl esters as described in European Pat. No. 0,012,463, Example II.

B8 Crosslinking agent based on a blocked isocyanate as described in German Published Application DAS No. 2,057,795, Experiment 6.

TABLE I

| Combination | Baking temperature °C. | | | | | | | | | | |
|---|---|---|---|---|---|---|---|---|---|---|---|
| | 90 | 100 | 110 | 120 | 130 | 140 | 150 | 160 | 170 | 180 | 190 |
| A1/B1 | — | — | — | — | 4 | 2 | 1 | — | — | — | — |
| A1/B4 | — | — | — | 4 | 3 | 1–2 | 1 | — | — | — | — |
| A1/B6 | — | — | 4 | 4 | 3 | 2 | 1–2 | 1 | — | — | — |
| A2/B1 | — | — | 4 | 3 | 1 | — | — | — | — | — | — |
| A2/B2 | — | 4 | 3 | 1 | — | — | — | — | — | — | — |
| A2/B3 | — | 4 | 3 | 1 | — | — | — | — | — | — | — |
| A2/B4 | — | — | 4 | 2–3 | 1 | — | — | — | — | — | — |
| A2/B5 | — | — | — | — | — | — | — | 4 | 3 | 1–2 | 1–2 |
| A2/B6 | — | — | — | — | — | — | — | — | 4 | 3 | 1–2 |
| A2/B7 | — | — | — | — | — | — | 4 | 2 | 1 | — | — |
| A2/B8 | — | — | — | — | — | — | 4 | 3–4 | 1–2 | 1 | — |
| A3/B2 | 4 | 2–3 | 1 | — | — | — | — | — | — | — | — |
| A3/B3 | 4 | 2–3 | 1–2 | 1 | — | — | — | — | — | — | — |
| A3/B5 | 4 | 2–3 | 1–2 | 1 | — | — | — | — | — | — | — |
| A3/B6 | 4 | 4 | 2–3 | 1–2 | 1 | — | — | — | — | — | — |
| A3/B7 | — | — | — | — | 4 | 3–4 | 2 | 1 | — | — | — |

Rating:
1 = no attack on surface
2 = slight swelling, slight roughening of the surface
3 = pronounced roughening of the surface
4 = rubbed through to the substrate

USE EXAMPLE 2

A surface coating formulation consisting of 70 parts, based on solids, of a commercial alkyd resin (Alkydal R40) as surface-coating binder A1 and (1) 30 parts of a commercial urea/formaldehyde surface coating resin in isobutanol (Plastopal FIB=crosslinking agent B6) or (2) 30 parts, based on solids, of a novel resin as described in Example 1 (crosslinking agent B1) and 50 parts of a TiO$_2$ white pigment (TiO$_2$ RH 57) is brought to a solids content of 50% with a mixture of 80 parts of xylene and 20 parts of glycol acetate and applied onto a degreased steel sheet by means of a 100 μm knife coater. The surface coating film is baked for 30 minutes at from 120° to 140° C. and then subjected to the tests described in Table II.

TABLE II

| | Combination | | | |
|---|---|---|---|---|
| | A1/B1 | | A1/B6 | |
| | 120° C. | 140° C. | 120° C. | 140° C. |
| Erichsen cupping (mm) | 9.2 | 8.8 | 9.0 | 8.5 |
| Konig pendulum hardness (sec) | 105 | 136 | 90 | 120 |
| Gloss, % reflectance/60° C. | 94 | 93 | 90 | 87 |
| Resistance to | | | | |
| xylene, rating | 1–2 | 1–2 | 2 | 1–2 |
| acetone, rating | 2 | 1–2 | 2 | 1–2 |

Rating:
1 = absolutely resistant
2 = slight swelling
3 = pronounced swelling
4 = not resistant

USE EXAMPLE 3

A mixture of 97 parts (based on solids) of a dip-coating binder (component A2) and 41 parts (based on solids) of a novel condensate according to Example 9 (component B4) is rendered water-dilutable by the addition of 3.4 parts of acetic acid and processed with fully deionized water to give a 12% strength aqueous dispersion (1150 parts). 137 parts of a 50% strength aqueous dispersion which contains 48 parts of a gray pigment consisting of carbon black and talc are added.

The mixture is stirred for 48 hours at from room temperature to 30° C. Coating films are deposited in the course of 2 minutes at 250 V on zinc-phosphatized steel specimen sheets which have been made the cathode, the said films are baked for 20 minutes at 110°, 120°, 130°, 140° and 160° C., and the resulting glossy surface coating films possessing good mechanical strength are tested with regard to solvent resistance by rubbing them forward and backward 50 times with a cottonwool ball soaked in acetone.

| Result | 110° C. | 120° C. | 130° C. | 140° C. | 160° C. |
|---|---|---|---|---|---|
| Combination A2/B4 | 4 | 1–2 | 1 | 1 | 1 |

Rating:
1 = not attacked
2 = slight roughening of the surface
3 = pronounced roughening of the surface
4 = rubbed away down to the substrate.

EXAMPLE 12

The condensate obtained as described in Example 7 is freed from isobutanol and dissolved in 100 parts of chloroform, and 208 parts of isophorone diisocyanate (IPDI) are added a little at a time at from 20° to 40° C. When the addition is complete, the mixture is refluxed for 1 hour, chloroform is distilled off, the resin-like residue is dissolved in 1200 parts of isobutanol and the organic phase is washed with water.

Concentrating the solution gives 1488 parts of 60.5% strength solution of the resin in isobutanol.

EXAMPLE 13

The condensate obtained as described in Example 8 is freed from isobutanol, and the pale yellow resinlike product is taken up in chloroform.

87 parts of toluylene diisocyanate (TDI) are added a little at a time to the resin solution obtained in this manner, the reaction mixture being kept at from 20° to 40° C. When the addition of TDI is complete, the mixture is stirred under reflux for 2 hours, after which chloroform is distilled off, the residue is taken up in isobutanol and the solution is concentrated to a solids content of about 65%. 845 parts of a pale yellow solution of the resin in isobutanol are obtained.

USE EXAMPLE 4

A coating formulation is prepared from 70 parts (based on solids) of one of the surface coating binders A1 or A2 below and 30 parts (based) on solids) of one of the novel reaction products B9 or B10 described in Examples 12 and 13 or, for comparison, commercial products B3 to B6.

The mixture of the two components is brought to about 50-60% strength with ethanol and applied onto a steel sheet by means of a 100 μm knife coater.

The coatings are then baked for 20 minutes at the temperatures stated in the Table. The surface coating films are tested by rubbing them 100 times with a cotton-wool ball soaked in acetone, and the results are reproduced in Table III.

A1 Commercial polyester-based surface coating binder (Alkydal® R40)

A2 Non-self-crosslinking cathodic binder, as described in Use Example 1.

B9 Novel reaction product according to Example 12.

B10 Novel reaction product according to Example 13.

For comparison

B5 Commercial melamine/formaldehyde surface coating resin, etherified with butanol (e.g. Luwipal® 015).

B6 Commercial urea/formaldehyde surface coating resin, etherified with isobutanol (e.g. Plastopal® FIB).

B7 Crosslinking agent based on β-hydroxyalkyl ester according to European Pat. No. 0,012,463, Example II.

B8 Crosslinking agent based on a blocked isocyanate as described in German Published Application DAS No. 2,057,795, Experiment 6.

TABLE III

| Combination | Baking temperature °C. | | | | | | | | | | |
|---|---|---|---|---|---|---|---|---|---|---|---|
| | 90 | 100 | 110 | 120 | 130 | 140 | 150 | 160 | 170 | 180 | 190 |
| A1/B9 | — | — | — | — | 4 | 2 | 1 | — | — | — | — |
| A1/B10 | — | — | — | — | 4 | 1-2 | 1 | — | — | — | — |
| A1/B6 | — | — | — | — | 4 | 2-3 | 1-2 | 1 | — | — | — |
| A2/B9 | — | — | 4 | 3 | 1 | — | — | — | — | — | — |
| A2/B10 | — | — | 4 | 2 | 1 | — | — | — | — | — | — |
| A2/B5 | — | — | — | — | — | — | — | 4 | 3 | 1-2 | 1-2 |
| A2/B6 | — | — | — | — | — | — | — | — | 4 | 3 | 1-2 |
| A2/B7 | — | — | — | — | — | — | — | 4 | 2 | 1 | — |
| A2/B8 | — | — | — | — | — | — | 4 | 3-4 | 1-2 | 1 | — |

Rating:
1 = no attack on surface
2 = slight swelling, slight roughening of the surface
3 = pronounced roughening of the surface
4 = rubbed through to the substrate

USE EXAMPLE 5

A surface coating formulation consisting of 70 parts, based on solids, of a commercial alkyd resin (Alkydal R40) as surface coating binder A1 and (1) 30 parts of a commercial urea/formaldehyde surface coating resin in isobutanol (Plastopal FIB, crosslinking agent B6) or (2) 30 parts, based on solids, of a novel resin according to Example 12 (crosslinking agent B9) and 50 parts of a TiO2 white pigment (TiO2 RH 57) is brought to a solids content of 50% with a mixture of 80 parts of xylene and 20 parts of glycol acetate and applied onto a degreased steel sheet by means of a 100 μm knife coater. The surface coating film is baked for 30 minutes at from 120° to 140° C. and then subjected to the tests described in Table IV.

TABLE IV

| | Combination | | | |
|---|---|---|---|---|
| | A1/B9 | | A1/B6 | |
| | 120° C. | 140° C. | 120° C. | 140° C. |
| Erichsen cupping (mm) | 9.4 | 8.6 | 9.2 | 8.5 |
| Konig pendulum hardness (sec) | 110 | 136 | 90 | 120 |
| Gloss, % reflectance/60° C. | 95 | 92 | 90 | 87 |
| Resistance to | | | | |
| xylene, rating | 1-2 | 1-2 | 2 | 1-2 |
| acetone, rating | 2 | 1-2 | 2 | 1-2 |

Rating:
1 = absolutely resistant
2 = slight swelling
3 = pronounced swelling
3 = not resistant

USE EXAMPLE 6

A mixture of 97 parts (based on solids) of a dipcoating binder (component A2) and 41 parts (based on solids) of a novel reaction product according to Example 12 (component B9) is rendered water-dilutable by the addition of 3.4 parts of acetic acid and processed with fully deionized water to give a 12% strength aqueous dispersion (1150 parts).

137 parts of a 50% strength aqueous dispersion which contains 48 parts of a gray pigment consisting of carbon black and talc are added.

The mixture is stirred for 48 hours at from room temperature to 30° C. Surface coating films are deposited in the course of 2 minutes at 250 V on zinc-phosphatized steel specimen sheets which have been made the cathode, the said films are baked for 20 minutes at 110°, 120°, 130°, 140° and 160° C., and the resulting glossy surface coating films possessing good mechanical strength are tested with regard to solvent resistance by rubbing them forward and backward 50 times with a cottonwool ball soaked in acetone.

| Result | 110° C. | 120° C. | 130° C. | 140° C. | 160° C. |
|---|---|---|---|---|---|
| Combination A2/B9 | 4 | 3 | 1-2 | 1 | 1 |

Rating:
1 = not attacked
2 = slight roughening of the surface
3 = pronounced roughening of the surface
4 = rubbed away down to the substrate.

EXAMPLE 14

(α) Preparation of a condensate which essentially contains structures of the formula

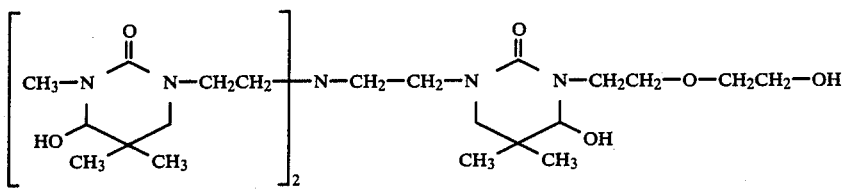

As described in Example 8, 176 parts of N,N'-dimethylurea, 60 parts of urea and 146 parts of tris-2-aminoethylamine are heated from 120° C. to 160° C. in the course of 3.5 hours, 105 parts of 2,2-aminoethoxyethanol are then added and heating is continued for a further 3 hours at temperatures increasing from 140° C. to 160° C. 200 parts of water and 50 parts of glacial acetic acid are then added. 225 parts of a 40% strength aqueous formaldehyde solution and 216 parts of isobutyraldehyde are added, after which the mixture is heated to the reflux temperature and 150 parts of concentrated nitric acid are added in the course of 20 minutes. During this procedure, the reflux temperature increases to about 100° C. The mixture is stirred for 2 hours at this temperature, and then cooled and neutralized with sodium hydroxide solution. To remove the salt, the reaction mixture is concentrated, the residue taken up in methanol, and the solution filtered and concentrated again.

(β) Preparation of the reaction product according to the invention: the concentrate obtained under (α) is taken up in 1000 parts of glacial acetic acid, and 220 parts of 1,2,4,5-benzenetetracarboxylic anhydride are added.

The mixture is stirred for 3 hours at 80° C., after which acetic acid is distilled off and the residue is taken up in isobutanol. The organic resin solution is washed acid-free and salt-free with water and sodium hydroxide solution and then concentrated to give 847 parts of a 62% strength solution of the resin in isobutanol.

USE EXAMPLE 7

A surface coating formulation is prepared from 70 parts (based on solids) of one of the surface coating binders A1 to A3 below and 30 parts (based on solids) of the novel reaction product B11 according to Example 14 or, for comparison, commercial products B5 to B8.

The mixture of the two components is brought to about 50–60% strength with ethanol and applied onto a steel sheet by means of a 100 μm knife coater.

The coatings are then baked for 20 minutes at the temperatures stated in the Table. The surface coating films are tested by rubbing them 100 times with a cotton-wool ball soaked in acetone, and the results are reproduced in Table V.

A1 Commercial polyester-based surface-coating binder (Alkydal® R 40).

A2 Non-self-crosslinking cathodic binder, as described in Use Example 1.

A3 OH-containing polyacrylate, as described in Use Example 1.

B11 = Novel condensate according to Example 14.

For comparison

B5 Commercial melamine/formaldehyde surface coating resin, etherified with butanol (eg. Luwipal® 015).

B6 Commercial urea/formaldehyde surface coating resin, etherified with isobutanol (eg. Plastopal® FIB).

B7 Crosslinking agent based on β-hydroxyalkyl esters according to European Pat. No. 0,012,463, Example II.

B8 Crosslinking agent based on a blocked isocyanate according to German Published Application DAS No. 2,057,795, Experiment 6.

TABLE V

| Combination | \multicolumn{11}{c}{Baking temperature °C.} |
|---|---|---|---|---|---|---|---|---|---|---|---|
| | 90 | 100 | 110 | 120 | 130 | 140 | 150 | 160 | 170 | 180 | 190 |
| A1/B11 | — | — | — | — | 4 | 2 | 1 | — | — | — | — |
| A2/B11 | — | — | 4 | 3 | 1 | — | — | — | — | — | — |
| A2/B5 | — | — | — | — | — | — | — | 4 | 3 | 1–2 | 1–2 |
| A2/B6 | — | — | — | — | — | — | — | — | 4 | 3 | 1–2 |
| A2/B7 | — | — | — | — | — | — | 4 | 2 | 1 | — | — |
| A2/B8 | — | — | — | — | — | — | 4 | 3–4 | 1–2 | 1 | — |
| A3/B11 | 4 | 2–3 | 1 | — | — | — | — | — | — | — | — |
| A3/B5 | 4 | 3 | 1–2 | 1 | — | — | — | — | — | — | — |
| A3/B6 | 4 | 3 | 1–2 | 1 | — | — | — | — | — | — | — |
| A3/B8 | — | — | — | — | 4 | 3–4 | 2 | 1 | — | — | — |

Rating:
1 = no attack on surface
2 = slight swelling, slight roughening of the surface
3 = pronounced roughening of the surface
4 = rubbed through to the substrate.

USE EXAMPLE 8

A surface coating formulation consisting of 70 parts, based on solids, of a commercial alkyd resin (Alkydal R40) as surface coating binder A1 and (1) 30 parts of a commercial urea/formaldehyde surface coating resin in isobutanol (Plastopal FIB = crosslinking agent B6) or (2) 30 parts, based on solids, of a novel resin as described in Example 14 (crosslinking agent B11) and 50 parts of a TiO₂ white pigment (TiO₂ RH 57) is brought to a solids content of 50% with a mixture of 80 parts of xylene and 20 parts of glycol acetate and applied onto a degreased steel sheet by means of a 100 μm knife coater. The surface coating film is baked for 30 minutes at from 120° to 140° C. and then subjected to the tests described in Table VI:

TABLE VI

| | Combination | | | |
|---|---|---|---|---|
| | A1/B11 | | A1/B6 | |
| | 120° C. | 140° C. | 120° C. | 140° C. |
| Erichsen cupping (mm) | 9.4 | 8.6 | 9.0 | 8.5 |
| Konig pendulum hardness (sec) | 108 | 146 | 90 | 122 |
| Gloss, % reflectance/60° C. | 94 | 90 | 90 | 87 |
| Resistance to | | | | |
| xylene, rating | 1-2 | 1-2 | 2 | 1-2 |
| acetone, rating | 1-2 | 1-2 | 2 | 1-2 |

Rating:
1 = absolutely resistant
2 = slight swelling
3 = pronounced swelling
4 = not resistant

EXAMPLE 15

(α) Preparation of a condensate which essentially contains structures of the formula

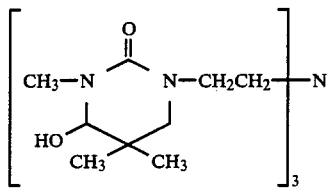

As described in Example 5, 292 parts of tris-2-aminoethylamine and 528 parts of N,N'-dimethylurea are stirred at 120° C. and 140° C. for 1 hour in each case, and then at 150° C. for 2 hours and finally at 160° C. for 0.5 hour, stirring being carried out under nitrogen. The viscosity of the reaction mixture increases substantially toward the end of the reaction. 350 parts of water and 50 parts of glacial acetic acid are then added, and the refluxed mixture is stired for 1 hour under nitrogen. Thereafter, 450 parts of formaldehyde (40% strength in water) and 144 parts of concentrated nitric acid are added and the mixture is heated at 65° C. 432 parts of isobutyraldehyde are then added dropwise sufficiently rapidly to keep the reaction mixture refluxing vigorously. The reflux temperature increases to about 103° C., and the mixture is stirred for 2 hours at this temperature. After the mixture has been cooled, it is brought to pH 3.5 with sodium hydroxide solution and 800 parts of butanol are added.

(β) Coupling with bisphenol A (preparation of the novel reaction product):

228 parts of bisphenol A are added, after which water is separated off in the course of 3 hours under atmospheric pressure at about 100° C., and the mixture is cooled and brought to pH 6.5 with sodium hydroxide solution, the aqueous phase is separated off and the organic phase is then washed with water and concentrated under reduced pressure to give 1538 parts of a 65% strength resin solution.

EXAMPLE 16

(α) Preparation of a condensate which essentially contains structures of the formula

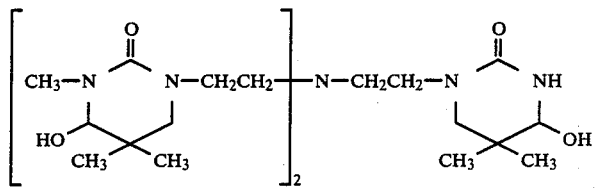

352 parts of N,N'-dimethylurea, 120 parts of urea and 292 parts of tris-2-aminoethylamine are heated to 120° C. in the course of 45 minutes and then heated continuously to 160° C. in the course of 3.5 hours, nitrogen being passed into the melt.

400 parts of water and 100 parts of glacial acetic acid are added, after which the mixture is cooled to 50° C., 450 parts of a 40% strength aqueous formaldehyde solution and 432 parts of isobutyraldehyde are added and the mixture is heated to the reflux temperature. After 240 parts of concentrated nitric acid have been added a little at a time, the temperature increases to 100° C. The mixture is stirred for 2 hours at this temperature, cooled and brought to pH 3.8 with sodium hydroxide solution, and 2000 parts of isobutanol are added.

(β) Coupling with the dimethylol compound of bisphenol A (preparation of the novel reaction product)

1000 parts of a solution, in isobutanol, of the product obtained by methylolating 1 mole of bisphenol A with 2 moles of formaldehyde are added to the resin solution produced under (α), and water is separated off for 3.5 hours. The mixture is cooled, the pH is brought to 7.0, the resin solution is washed with twice 1000 parts of water and the organic phase is concentrated to give 1780 parts of a solution of the resin in isobutanol, the content of solid resin in the solution being 68%.

USE EXAMPLE 9

A coating formulation is prepared from 70 parts (based on solids) of one of the surface coating binders A1 to A3 below and 30 parts (based on solids) of one of the novel reaction products B12 or B13 described in Examples 15 and 16 or, for comparison, commercial products B5 to B8.

The mixture of the two components is brought to about 50-60% strength with ethanol and applied onto a steel sheet by means of a 100 pm knife coater.

The coatings are then baked for 20 minutes at the temperatures stated in the Table. The surface coating films are tested by rubbing them 100 times with a cotton-wool ball soaked in acetone, and the results are reproduced in Table VII.

A1 Commercial polyester-based surface coating binder (Alkydal ® R40)

A2 Non-self-crosslinking cathodic binder, as described in Use Example 1.

A3 OH-containing polyacrylate, as described in Use Example 1.

B12 Novel reaction product according to Example 15.

B13 Novel reaction product according to Example 16.

For comparison

B5 Commercial melamine/formaldehyde surface coating resin, etherified with butanol (e.g. Luwipal ® 015).

B6 Commercial urea/formaldehyde surface coating resin, etherified with isobutanol (e.g. Plastopal ® FIB).

B7 Crosslinking agent based on β-hydroxyalkyl esters as described in European Pat. No. 0,012,463, Example II.

B8 Crosslinking agent based on a blocked isocyanate as described in German Published Application DAS No. 2,057,795, Experiment 6.

TABLE VII

| Combination | Baking temperature °C. | | | | | | | | | | |
|---|---|---|---|---|---|---|---|---|---|---|---|
| | 90 | 100 | 110 | 120 | 130 | 140 | 150 | 160 | 170 | 180 | 190 |
| A1/B12 | — | — | — | — | 4 | 2 | 1 | — | — | — | — |
| A1/B13 | — | — | — | 4 | 3 | 1-2 | 1 | — | — | — | — |
| A1/B6 | — | — | — | 4 | 3-4 | 2-3 | 1-2 | — | — | — | — |
| A2/B12 | — | — | 4 | 3 | 1 | — | — | — | — | — | — |
| A2/B13 | — | — | 4 | 2-3 | 1 | — | — | — | — | — | — |
| A2/B5 | — | — | — | — | — | — | — | 4 | 3 | 1-2 | 1-2 |
| A2/B6 | — | — | — | — | — | — | — | — | 4 | 3 | 1-2 |
| A2/B7 | — | — | — | — | — | — | 4 | 2 | 1 | — | — |
| A2/B8 | — | — | — | — | — | — | 4 | 3-4 | 1-2 | 1 | — |
| A3/B12 | 4 | 2-3 | 1 | — | — | — | — | — | — | — | — |
| A3/B13 | 4 | 2-3 | 1-2 | 1 | — | — | — | — | — | — | — |
| A3/B5 | 4 | 2-3 | 2 | 1-2 | 1 | — | — | — | — | — | — |
| A3/B6 | 4 | 4 | 2-3 | 1-2 | 1 | — | — | — | — | — | — |
| A3/B8 | — | — | — | — | — | — | 4 | 4 | 2-3 | 1 | — |

Rating:
1 = no attack on surface
2 = slight swelling, slight roughening of the surface
3 = pronounced roughening of the surface
4 = rubbed through to the substrate.

USE EXAMPLE 10

A surface coating formulation consisting of 70 parts, based on solids, of a commercial alkyd resin (Alkydal R40) as surface coating binder A1 and (1) 30 parts of a commercial urea/formaldehyde surface coating resin in isobutanol (Plastopal FIB=crosslinking agent B6) or (2) 30 parts, based on solids, of a novel resin as described in Example 15 (crosslinking agent B12) and 50 parts of a TiO$_2$ white pigment (TiO$_2$ RH 57) is brought to a solids content of 50% with a mixture of 80 parts of xylene and 20 parts of glycol acetate and applied onto a degreased steel sheet by means of a 100 μm knife coater. The surface coating film is baked for 30 minutes at from 120° to 140° C. and then subjected to the tests described in Table VIII.

TABLE VIII

| | Combination | | | |
|---|---|---|---|---|
| | A1/B12 | | A1/B6 | |
| | 120° C. | 140° C. | 120° C. | 140° C. |
| Erichsen cupping (mm) | 9.0 | 8.7 | 9.0 | 8.5 |
| Konig pendulum hardness (sec) | 105 | 144 | 90 | 120 |
| Gloss, % reflectance/60° C. | 94 | 93 | 90 | 87 |
| Resistance to xylene, rating | 1-2 | 1-2 | 2 | 1-2 |

TABLE VIII-continued

| | Combination | | | |
|---|---|---|---|---|
| | A1/B12 | | A1/B6 | |
| | 120° C. | 140° C. | 120° C. | 140° C. |
| acetone, rating | 1-2 | 1-2 | 2 | 1-2 |

Rating:
1 = absolutely resistant
2 = slight swelling
3 = pronounced swelling
4 = not resistant

USE EXAMPLE 11

A mixture of 97 parts (based on solids) of a dip-coating binder (component A2) and 41 parts (based on solids) of a novel condensate according to Example 15 (component B12) is rendered water-dilutable by the addition of 3.4 parts of acetic acid and processed with fully deionized water to give a 12% strength aqueous dispersion (1150 parts). 137 parts of a 50% strength aqueous dispersion which contains 48 parts of a gray pigment consisting of carbon black and talc are added.

The mixture is stirred for 48 hours at from room temperature to 30° C. Coating films are deposited in the course of 2 minutes at 250 V on zinc-phosphatized steel specimen sheets which have been made the cathode, the said films are baked for 20 minutes at 110°, 120°, 130°, 140° and 160° C., and the resulting glossy surface coating films possessing good mechanical strength are tested with regard to solvent resistance by rubbing them forward and backward 50 times with a cottonwool ball soaked in acetone.

| Result | 110° C. | 120° C. | 130° C. | 140° C. | 160° C. |
|---|---|---|---|---|---|
| Combination A2/B12 | 4 | 2-3 | 1-2 | 1 | 1 |

Rating:
1 = not attacked
2 = slight roughening of the surface
3 = pronounced roughening of the surface
4 = rubbed away down to the substrate.

We claim:

1. A condensate which essentially contains substituted propyleneureas of the formulae (I) and/or (II)

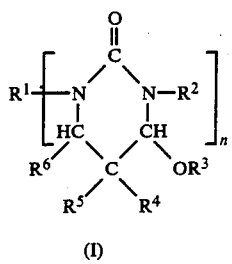
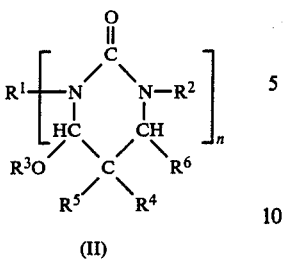

where $R^1$ is a divalent or polyvalent, straight-chain or branched alkylene, cycloalkylene, oxaalkylene or azaalkylene radical of 4 to 60 carbon atoms which may contain one or more hydroxyl groups and/or urea substituted by hydroxyalkyl, hydroxycycloalkyl, hydroxyoxaalkyl and/or hydroxyazaalkyl, $R^2$, $R^3$, $R^4$, $R^5$ and $R^6$ are identical or different and are each hydrogen, alkyl of 1 to 18 carbon atoms, cycloalkyl of 5 to 15 carbon atoms or oxaalkyl or azaalkyl, each of 2 to 18 carbon atoms, and R2 may furthermore be hydroxyalkyl, with the proviso that where R2 is hydroxyalkyl the latter is of 4 to 18 carbon atoms and n is from 2 to 20, and the individual radicals $R^2$, $R^3$, $R^4$, $R^5$ and $R^6$ of the n propyleneurea units of the formulae (I) and/or (II) may be identical or different while conforming to the stated definitions.

2. A process for the preparation of a condensate as defined in claim 1, wherein first (a) primary polyamines of the formula (III)

are reacted with (b) from 1.0 to 1.5 moles per primary amino group of the amine of urea or monosubstituted or symmetrically disubstituted ureas of the formula (IV) $R^2NH-CO-NHR^2$ at from 100° to 200° C., in the presence of monoalkanolamines, and the resulting products are reacted with (d) from 1.4 to 2.5 moles of one or more aldehydes of the formula (V)

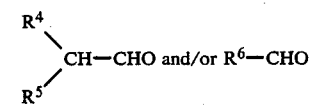

per mole of urea (b) in the presence of an acidic catalyst at from 50° to 150° C., in the presence or absence of a solvent, with the proviso that not less than 0.7 mole of an aldehyde (d) which contains one or more hydrogen atoms α to the aldehyde group is used per mole of urea (b) employed, $R^1$ to $R^6$ and n having the meanings stated in claim 1.

3. A process for the preparation of a condensate as defined in claim 1 wherein (a) primary monoamines of the formula (VII),

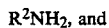

and (e) polyisocyanates of the formula (IX)

or (a) primary polyamines of the formula (III)

and (e) monoisocyanates of the formula (VIII), $R^2-NCO$, are first reacted in an aqueous medium at form about 0° to 120° C. from about 0.5 to 6 hours in a molar ratio of form 0.8 to 1.1 moles of isocyanate per mole of primary amino group, and the resulting polyureas are reacted with (d) from 1.4 to 2.5 moles of one or more aldehydes per mole of the urea units formed in the reaction of (a) with (e), in the presence of an acidic catalyst at from 50° to 150° C. and in the presence or absence of a solvent, with the proviso that not less than 0.7 mole of one or more aldehydes (d) which contain one or more hydrogen atoms α to the aldehyde group is used per mole of the urea units formed by reacting (a) with (e), $R^1$ to $R^6$ and n having the meanings stated in claim 1.

4. The process of claim 3, wherein isobutyraldehyde or a mixture of isobutyraldehyde with formaldehyde is used as the aldehyde (d).

* * * * *

UNITED STATES PATENT AND TRADEMARK OFFICE
CERTIFICATE OF CORRECTION

PATENT NO. : 4,855,394

DATED : August 8, 1989

INVENTOR(S) : Ulrich GOECKEL et al.

It is certified that error appears in the above-identified patent and that said Letters Patent is hereby corrected as shown below:

On the title page, Foreign Application Priority Data shoud read

-- July 17, 1985 [DE] Fed. Rep. of Germany ... 3525438
July 17, 1985 [DE] Fed. Rep. of Germany ... 3525434
July 17, 1985 [DE] Fed. Rep. of Germany ... 3525435
July 17, 1985 [DE] Fed. Rep. of Germany ... 3525437 --

IN THE CLAIMS

Claim 1: column 33, lines 24 and 25,

"R2" should read $--R^2--$

Claim 3: column 34, line 22 should read $--R^1\text{\textlbrackdbl}NCO]_n$ or--

Claim 3: column 34, line 30

"at form about" should read --at from about--.

Signed and Sealed this

Fourth Day of September, 1990

Attest:

HARRY F. MANBECK, JR.

*Attesting Officer*  *Commissioner of Patents and Trademarks*